United States Patent
Eger et al.

(10) Patent No.: US 9,949,661 B2
(45) Date of Patent: Apr. 24, 2018

(54) SIGNAL PROCESSING UNIT OF AN EMG MEASURING SYSTEM

(71) Applicant: Dräger Medical GmbH, Lübeck (DE)

(72) Inventors: Marcus Eger, Lübeck (DE); Frank Sattler, Lübeck (DE); Jian Hua Li, Lübeck (DE); Wanja Sebastian Schöpfer, Lübeck (DE); Carsten Leischner, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 190 days.

(21) Appl. No.: 14/744,525

(22) Filed: Jun. 19, 2015

(65) Prior Publication Data

US 2015/0366480 A1 Dec. 24, 2015

(30) Foreign Application Priority Data

Jun. 20, 2014 (DE) .................. 10 2014 008 841

(51) Int. Cl.
*A61B 5/00* (2006.01)
*A61B 5/0492* (2006.01)
(Continued)

(52) U.S. Cl.
CPC .......... *A61B 5/0492* (2013.01); *A61B 5/0004* (2013.01); *A61M 16/00* (2013.01);
(Continued)

(58) Field of Classification Search
CPC .. A61M 16/00; A61M 16/01; A61M 16/0069; A61M 16/202; A61M 2205/3651; A61M 2205/3592; A61M 2205/3303; A61M 2205/8206; A61M 2230/0005; A61M 2230/10; A61M 2230/60; A61M 2230/432; A61M 2016/0024; A61M 2016/0027; A61M 2016/0039; A61B 5/0006; A61B 5/0004; A61B 5/04012; A61B 5/0492; A61B 5/0205;
(Continued)

(56) References Cited

U.S. PATENT DOCUMENTS

| 6,411,843 B1 * | 6/2002 | Zarychta ............. A61B 5/0488 128/204.23 |
| 2004/0133123 A1 * | 7/2004 | Leonhardt ............. A61B 5/026 600/547 |

(Continued)

FOREIGN PATENT DOCUMENTS

| DE | 10 2012 003 509 A1 | 8/2013 |
| EP | 2 371 412 B1 | 7/2013 |

*Primary Examiner* — Mallika D Fairchild
(74) *Attorney, Agent, or Firm* — McGlew and Tuttle, P.C.

(57) ABSTRACT

An EMG measuring system has a signal processing unit (8) and with at least one electrode (4) for measuring a potential difference in a muscle, a muscle fiber or in a skin area of a patient. At least one measured signal representing the potential difference is transmitted from the electrode (4) to the signal processing unit (8). Another signal, which is transmitted to the at least one external device (9), is generated in the signal processing unit (8) on the basis of this measured signal. A signal transmitted from the at least one external device (9) is processed by the signal processing unit (8) and at least one control signal is generated on the basis of this signal.

20 Claims, 1 Drawing Sheet

(51) Int. Cl.
*A61M 16/00* (2006.01)
*A61M 16/01* (2006.01)

(52) U.S. Cl.
CPC ..... *A61M 16/01* (2013.01); *A61M 2016/0024* (2013.01); *A61M 2016/0027* (2013.01); *A61M 2016/0039* (2013.01); *A61M 2205/18* (2013.01); *A61M 2205/3561* (2013.01); *A61M 2205/3592* (2013.01); *A61M 2205/8206* (2013.01); *A61M 2230/432* (2013.01); *A61M 2230/60* (2013.01)

(58) Field of Classification Search
CPC ..... A61B 5/0402; A61B 5/7203; A61B 5/742; A61B 5/7475; A61B 2562/222; A61B 2560/0475; A61B 2560/18
See application file for complete search history.

(56) References Cited

U.S. PATENT DOCUMENTS

| | | | |
|---|---|---|---|
| 2008/0200966 A1* | 8/2008 | Blomberg | A61M 16/00 607/42 |
| 2008/0308104 A1 | 12/2008 | Blomberg et al. | |
| 2010/0319691 A1* | 12/2010 | Lurie | A61M 16/0012 128/203.12 |
| 2012/0152251 A1* | 6/2012 | Eger | A61M 16/0051 128/204.23 |

* cited by examiner

SIGNAL PROCESSING UNIT OF AN EMG MEASURING SYSTEM

CROSS REFERENCE TO RELATED APPLICATIONS

This application claims the benefit of priority under 35 U.S.C. § 119 of German Patent Application DE 10 2014 008 841.3 filed Jun. 20, 2014, the entire contents of which are incorporated herein by reference.

FIELD OF THE INVENTION

The present invention pertains to an electromyogram (EMG) measuring system with a signal processing unit, which makes communication possible between the EMG measuring system and at least one additional external device. The EMG measuring system has at least two electrodes for measuring a potential difference in a muscle, a muscle fiber and/or in a skin area of a patient, wherein at least one measured signal representing the potential difference or a change in a potential difference can be transmitted to the signal processing unit. The signal processing unit is designed such that an additional signal can be generated on the basis of the measured signal and transmitted to at least one external device, especially a display unit or a ventilator (also known as a respirator).

BACKGROUND OF THE INVENTION

Electromyography (EMG) is an electrophysiological method in neurological diagnostics, in which the electrical activity of muscles is measured. Superimpositions of the action potentials of many muscle fibers as well as of changes thereof are often detected by means of concentric surface electrodes. Individual muscle fibers can also be detected with special needles, and measurements of the changes of potential differences on the skin are also possible with surface electrodes. The electrical activities, which originate, as a rule, from different muscles, are detected during the performance of an EMG.

As soon as a muscle contracts, this is detected on the basis of action potentials. If an EMG is carried out while a patient is being ventilated, it should be borne in mind that the patient is active in respect to his respiratory muscles, as long as he is breathing spontaneously at least partially. The patient must not be ventilated mandatorily in these cases, but the ventilation, especially the ventilator, must be synchronized with the spontaneous activity caused by the effort of the respiratory muscles.

Besides the use of electromyography to recognize myopathies and neuropathies, a system for assisting the mechanical ventilation of a patient is known, in which EMG signals are used. In a NAVA® system (Neurally Adjusted Ventilatory Assist), the ventilator is controlled as a function of the electrical activity of the diaphragm (Edi), which is detected by means of a special gastric catheter. Ventilatory assist, which takes place synchronously and proportionally to the patient's respiratory demand, is achieved here by varying the respiratory pressure generated by the ventilator, taking into account the amplitude and duration of the activity of the diaphragm (Edi). The patient's respiratory activity shall be assisted with this system by the ventilator assuming a necessary part of the respiratory work and thus ensuring that the patient is not needlessly exhausted or becomes tired. In view of the increase of chronic lung diseases and the need for improved therapy, such a ventilatory assist with improved interaction between patient and ventilator drive is an important requirement on modern ventilation systems.

Respiratory monitoring as well as ventilation control, especially ventilator control, based on signals of a surface EMG, are known as well. Such an EMG measuring system usually has an EMG front end, which is unidirectionally connected with a display, diagnostic or therapeutic device via a galvanic, wireless or optical signal connection.

A ventilation system for the non-invasive ventilation with a ventilator, which is controlled by a control unit, and with a patient module with electrodes for deriving electrode signals from the signal of a patient's chest, is known from DE 10 2012 003 509 A1. The control device according to the technical embodiment described is designed such that ECG signal components are suppressed in the electrode signals in order to obtain the electromyographic signals (EMG signals) representing the respiratory effort and to control the ventilator drive as a function of these EMG signals. It is thus possible by means of the technical means for accomplishing the object of the invention described to derive EMG signals from the electrode signals obtained, and to take these into account during the mechanical ventilation of a patient, on the one hand, and to record ECG signals and to make data representative of the ECG available for display, on the other hand.

Furthermore, EP 2 371 412 B1 discloses a ventilation or anesthesia system, which is coupled with an EMG measuring system, wherein signals, which are used as the basis for the mechanical ventilation, are provided by the EMG measuring system or a control device of this system. The control unit of the EMG system has an analog-digital conversion unit here, with which analog electromyographic muscle activity detected by the at least one sEMG sensor can be converted into digital signals. Since the at least one sensor detects only very low voltages from the respiratory muscles, so that the corresponding low voltages may be distorted when these very weak currents are being sent over rather great distances to an external control unit, a corresponding conversion already in the control unit arranged close to the patient is useful. The control device of the EMG measuring system can be identified by a higher-level control device, which is arranged especially within the ventilator. Suitable identification data are stored for this in the EMG front end.

The EMG front end modules arranged close to the patient, which are known from the state of the art, thus often have components for the digitization, preprocessing and transmission of the EMG signals as well as for supplying the module with energy. Furthermore, elements for signal processing are provided, e.g., for forming the difference, filtering, removing artifacts, above all of the electrical cardiac activity (ECG), and for calculating the enveloping curve. However, the drawback of the prior-art EMG front end modules is that a plurality of functions for measurement, signal processing, signal transmission, generation of control signals and for displaying measured values and of values derived therefrom are distributed among different medical devices.

On the one hand, many different devices are thus often arranged, especially in intensive care, and, on the other hand, the complexity of the overall system and hence of the possible source of risk during the wiring of the devices as well as the analysis of corresponding measured values is increased hereby. Likewise, the effort for the maintenance and verification of such systems with their different components is also relatively complicated.

Thus, a large number of parameters have had to be hitherto neglected or entered separately on a conventionally unidirectionally connected EMG front end module for cardiorespiratory analysis or for signal generation for controlling the ventilation. All the information is potentially available if the EMG functionality is integrated in the control unit of the ventilator, as is known from the state of the art; however, there arises the disadvantage of a self-contained device. As a result, the flexibility, especially the usability of the EMG functionality for patient monitoring, is reduced or simply impossible. Such a central structure also has disadvantages concerning the possibility of maintenance and software complexity.

SUMMARY OF THE INVENTION

Based on the means for accomplishing an object of the inventions known from the state of the art as well as the above-described problems, a basic object of the present invention is to perfect an EMG measuring system such that EMG signals can be detected, processed and made available for actuating external devices in a relatively simple manner. It would be especially advantageous in this connection if the largest possible number of functions from the area of the cardiorespiratory monitoring and the EMG-controlled ventilation of a patient can be combined in one device. The bundling of a plurality of functions with suitable signal processing in one device shall reduce especially the load of the processors of external devices, for example, a ventilator or monitor, so that these are not burdened with secondary tasks.

An EMG measuring system of this class has a signal processing unit and at least two electrodes for measuring a potential difference in a muscle, a muscle fiber and/or in a skin area of a patient. At least one measured signal representing the potential difference can be transmitted in this case from the electrodes, especially surface electrodes, to the signal processing unit, and an output signal, which can be transmitted to at least one external device, especially a display unit and/or a ventilator, can be generated in the signal processing unit on the basis of the measured signal. Such an EMG measuring system has been perfected according to the present invention such that a signal transmitted from the one external device can be processed by the signal processing unit and at least one control signal can be generated on the basis of this signal. The essential advantage of the EMG measuring system according to the present invention is consequently that a signal processing unit, which is preferably arranged close to the patient, is provided, in which not only measured signals can be converted for improved transmission, but in which at least one control signal can be generated both on the basis of the measured values detected by the EMG measuring system itself and the measured signals corresponding to these and on the basis of external data and/or signals. It is advantageously conceivable in this case that the control signal is, in turn, used as the basis for the measurement of potential differences or corresponding changes in a muscle, a muscle fiber and/or in a skin area of the patient and/or is transmitted to an external device, especially to a display unit or to a ventilator. Thus, an EMG measuring system with a signal processing unit is provided, in which a plurality of functions, which were hitherto distributed among different devices, are combined. In particular, the display of measured values or of values derived therefrom on a patient monitor or even the actuation of a ventilator on the basis of control signals, which were generated in the signal processing unit of the EMG measuring system, is possible.

By providing a signal processing unit designed according to the present invention, an EMG measuring system is provided, in which functions that pertain to the cardiorespiratory monitoring and the EMG-controlled ventilation of a patient are preferably realized. Based on the integration of corresponding functionalities in the signal processing unit of an EMG measuring system, corresponding functions, especially for generating suitable control signals, can be prevented from being distributed among different external devices, for example, a conventional EMG front end, a ventilator and a patient monitor, which ultimately means a great effort concerning the software architecture and software updating and in connection with the performance of maintenance and tests.

The processor load in external devices, especially of the ventilator or of a patient monitor, can thus be preferably reduced by generating control signals within a signal processing unit of the EMG measuring system. It is conceivable in this case, in an especially preferred manner, that at least one control signal, which affects the measurement of potential differences according to the needs by means of the electrodes arranged on the patient and/or the function of the external device, is generated in the signal processing unit on the basis of measured signals of the needle electrodes and/or by taking into account signals that were transmitted from at least one external device.

Provisions are made, furthermore, in a special variant of the present invention for the signal processing unit to be suitable for a bidirectional data exchange with the at least one external device. It is essential in this case that the signal processing unit of an EMG measuring system designed according to the present invention can receive at least one data set or a signal from an external device, especially from a ventilator and/or a patient monitor via a suitable interface and these data or this signal can be processed further in the signal processing unit. It is conceivable, in principle, in this connection that a data exchange between the signal processing unit of the EMG measuring system and at least one external device is carried out as a wired or wireless exchange, especially via WLAN or Bluetooth.

At least one control signal can be generated for actuating a ventilator in the signal processing unit in a special embodiment of the present invention and can be transmitted to the ventilator. The signal processing unit of the EMG measuring system is able in this case to generate a control signal taking into account measured values or measured signals and/or data, for example, patient-specific data and/or other signals, which the control unit has received from external devices. It is possible, by means of such a control signal, both to initiate or affect the measurement of a potential difference, including possible changes in a muscle, a muscle fiber and/or in a skin area of a patient and to actuate an external device, for example, a ventilator and/or a patient monitor in the desired manner. An EMG measuring system designed according to the present invention is able to detect electromyographic signals, to generate corresponding measured values and to convert them into digital signals. Such an EMG measuring system can, moreover, generate control signals that can be used by the EMG measuring system itself or by external medical devices that are connected to the EMG measuring system. At least one ventilator and/or a valve of a ventilator and/or anesthesia device is advantageously actuated by means of such a control signal generated in the signal processing unit of the EMG measuring system. It is expressly pointed out in this connection that the function of a ventilator is integrated in modern anesthesia devices in order to make it possible to mechanically ventilate a patient during the anesthesia. It is therefore likewise conceivable to couple an EMG measuring system designed according to the present invention, especially its signal processing unit, with an anesthesia device in terms of data processing and to actuate the anesthesia device, at least from time to time and/or as needed, by means of control signals that are generated in the control unit of the EMG measuring system.

It is conceivable according to a special variant of the present invention that at least one control signal can be generated in the signal processing unit for actuating a patient monitor and it can be transmitted to the patient monitor via a suitable interface. Control signals are advantageously generated by the signal processing unit in this case, so that measured values and/or other values or information, which are derived from the recorded measured values, especially electromyographic signals, can be displayed on the monitor.

At least one control signal, by which the at least one component of the EMG measuring system itself can be actuated, is advantageously generated in the signal processing unit of the EMG measuring system. At least one time and/or a time interval, in which the measurement of a potential difference takes place, can be preferably determined in the signal processing unit on the basis of data transmitted by the at least one external device to the signal processing unit. If an EMG measuring system designed in such a manner according to the present invention is combined with a ventilator, it is preferably conceivable that the measurement of a muscle activity, especially of an activity of the diaphragm, is synchronized with the ventilation of the patient. A measurement is preferably performed in this case as soon as the patient has ended exhalation and starts inhaling. If the active ventilation is stopped at a suitable time or the inhalation valve as well as the exhalation valve are closed, the electrical activity of the diaphragm muscles can be measured by means of the EMG sensors, on the one hand, and a vacuum, which is generated by the muscle activity in the airways, can be measured by means of sensors in the breathing air circuit, on the other hand Based on these data, it is possible in an especially suitable manner to adapt the ventilator to the respiratory activity of the patient being mechanically ventilated and to synchronize it with the respiratory activity.

In a special variant of the present invention, the EMG measuring system is capable of sending electric signals to the signal processing unit, which are separated into EMG and ECG signals there. It is possible in this way to separate the received electrode signals into signals that are due to the activity of the diaphragm, on the one hand, and are due to the cardiac activity, on the other hand.

Further, it is advantageously conceivable that data or signals that are transmitted from the at least one external device to the signal processing unit can be stored and/or processed in the signal processing unit. Thus, both the processing of patient-specific data stored in the signal processing unit or in a memory of the EMG measuring system, which memory is associated with this unit, and of measured values that were recorded by external devices, is conceivable, either separately or together. It is, furthermore, conceivable in this connection that the EMG measuring system has an input unit, especially a keyboard or a touch screen, via which corresponding data are made available to a memory unit and/or to the signal processing unit of the EMG measuring system. It is, of course, likewise conceivable that corresponding data are scanned or entered automatically and/or transmitted to the signal processing unit and/or to a memory via a suitable interface of the EMG measuring system.

According to an especially preferred variant of the present invention, an EMG measuring system designed according to the present invention can be used within the framework of the cardiorespiratory monitoring of a ventilated patient. It is conceivable in this connection that certain electric signals, which are generated on the basis of the cardiac or myocardial or respiratory muscle activity, are likewise stored and/or processed in the signal processing unit of the EMG measuring system. Additional information, which is based, e.g., on pneumatic signals, e.g., information on breaths and/or respiratory signals, e.g., flow, pressure and/or $CO_2$ content, is likewise stored in a memory unit of the EMG measuring system and/or used in the signal processing unit without intermediate storage to generate at least one control signal in order to thus improve the validity, quality and robustness of the cardiorespiratory monitoring. The mechanically ventilation of a patient can likewise be improved considerably in this way by the use of additional information.

If an EMG measuring system designed according to the present invention is connected to a patient monitor, it is preferably conceivable that special, patient-specific data, e.g., the oxygen saturation of the blood and/or impedance values of the thorax, are taken into account when generating at least one control signal in the signal processing unit. If the connection is established additionally or separately to a ventilator, it is, further, conceivable to use ventilation-specific parameters, for example, the inspiratory oxygen concentration and/or values set or stored in the ventilator as well as modes of ventilation, as the basis for generating a control signal.

A relatively accurate cardiorespiratory analysis, identification of the ventilation drive, detection and assessment of asynchronisms, plausibility tests, alarm generation or calculation of signal qualities can be preferably performed based on the availability of a plurality of data, as they were mentioned as examples above, in the signal processing unit of the EMG measuring system designed according to the present invention. It is likewise conceivable, in principle, to determine the status of the patient, for example, the degree of his exhaustion, in order to make it possible to make the most accurate predictions and/or recommendations possible for actions to be performed in the future, e.g., a planned extubation. Furthermore, an EMG measuring system designed according to the present invention makes possible an advantageous therapy or diagnostic procedure tailored to the patient, because the information, which is otherwise distributed to different external devices and/or is present in the hospital information system, especially patient-specific parameters, such as age, gender, body weight, clinical picture and patient status, are available in one device.

An EMG front end as part of an EMG measuring system, which has a signal processing unit designed in a suitable manner and, furthermore, at least one memory, which is designed to receive the information mentioned above, combines a plurality of functions, which are otherwise distributed to different medical devices. The technical means for accomplishing the object of the invention according to the present invention thus ensures that the detection of electromyographic signals and the use of these signals in the therapy and monitoring of a patient can be integrated in an overall system in a preferred manner. Such a central structure has, furthermore, considerable advantages in terms of the possibility of maintenance and software architecture.

To achieve suitable communication of the EMG measuring system, above all the signal processing unit thereof as well as of the memories, which may possibly be provided, with external devices, especially with ventilators and/or patient monitors, one or more alternative interfaces, e.g., LAN, RS232, RS485, SPI, CAN, I2C or analogous interfaces, are implemented in the EMG measuring system. As an alternative or in addition, interfaces for wireless data communication, e.g., Bluetooth, ZigBee. and/or WLAN, may be provided as well. The provision of different interfaces on an EMG measuring system offers in this case the advantage that the EMG measuring system can be combined with a plurality of different devices and the interface that is optimal for the application is available depending on which external device is used. Such an interface is located, depending on the arrangement of the signal processing unit, either between the electrode cable leading to the patient and the signal processing unit or between the signal processing unit and the external device. The communication between the EMG measuring system and at least one external medical device takes place bidirectionally via the aforementioned interface, whereby a wired information and energy transmission is preferably achieved.

In a special embodiment, the EMG measuring system has an EMG front end, to which the at least one electric cable leading with the EMG electrodes can be connected. Further, the EMG front end preferably has a module, by which preprocessing of the EMG measured signals received is performed, whereby the measured signals are especially amplified and converted into digital signals.

According to a further special embodiment of the EMG measuring system according to the present invention, galvanic separation is provided between the EMG measuring system and the at least one external device. It is conceivable in this connection to provide the galvanic separation in relation to the signal processing unit either between the signal preprocessing and the main signal processing or between the signal processing and the at least one external device. The galvanic separation is preferably embodied within the EMG front end arranged close to the patient behind the module for signal processing. The arrangement of a galvanic separation between the unit for signal preprocessing and the signal processing unit for generating at least one control signal is especially advantageous in respect to the development of heat. If the signal processing unit is likewise arranged in or at the EMG front end, it is likewise conceivable to provide the galvanic separation between the signal processing unit and the external device. However, it must be borne in mind in this case that the value of the coupling capacity present in the external device is taken into account when selecting the coupling capacity in order to ensure sufficient galvanic separation.

Galvanic separation with low coupling capacity, especially with at least one DC-DC coupler with low coupling capacity, is preferably embodied between the EMG measuring system and an external medical device. It is conceivable in this connection, as an alternative or in addition, to use an optocoupler. The use of a low coupling capacity is especially advantageous because the common mode current flowing through the common electrode and hence the sensitivity to common mode interferences depend on this. A corresponding coupling capacity is preferably lower than 50 pF, especially lower than 40 pF, and especially preferably lower than 12 pF. A coupling capacity that is lower than 10 pF is used in a very special embodiment.

A special advantage of the technical means for accomplishing the object of the invention according to the present invention, which provides for transferring the signal processing for generating control signals into the signal processing unit of the EMG measuring system, is, furthermore, that the necessary calculations can be carried out with an optimal scanning frequency, which cannot usually be obtained on a connected ventilator and/or patient monitor, especially if no comparably high-frequency calculations can be performed on the corresponding device. It is, further, possible by the integration of different calculation and data processing steps in the signal processing unit of the EMG measuring system to drastically reduce the time delays compared to prior-art systems in time-critical signal processing steps. Based on the integration of different functionalities, which have hitherto been distributed to different devices, a device is obtained that is a single device at least virtually according to function and that can be substantially better optimized.

Furthermore, it is conceivable that the resulting data rate of the EMG measuring system, especially of the signal processing unit to the external device, is reduced compared to prior-art systems based on the signal processing taking place in the signal processing unit.

It is, furthermore, conceivable according to a very special embodiment of the present invention that the EMG measuring system has an energy storage device, especially a battery, so that the system can be operated at least occasionally autarchically from an external power supply.

The present invention will be explained in more detail below without limitation of the general idea of the invention based on exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
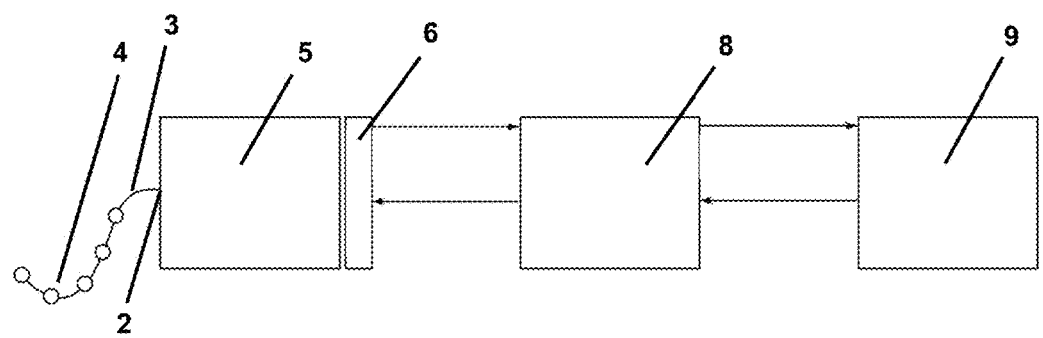
FIG. 1 is a block diagram for the schematic representation of a system for cardiorespiratory monitoring or for an EMG-based control of a ventilator.

Referring to the drawings, FIG. 1 shows a block diagram of an EMG measuring system, which is coupled with a ventilator 9 for the mechanical ventilation of a patient as well as for monitoring the patient. The EMG electrodes 4 arranged on the patient are connected via an electrode cable 3 with a terminal 2 of the EMG front end 1. Further, the EMG measuring system has a signal processing unit 8 for generating at least one control signal on the basis of the detected EMG signals. An essential technical feature of this signal processing unit 8 is that it is suitable for bidirectional data exchange with the EMG front end 1 as well as with the ventilator 9. The data exchange between the EMG measuring system and the ventilator 9 takes place in the example being shown via an RS-232 interface, and the signal processing unit 8 receives, on the one hand, raw EMG signals and status signals from the EMG front end, and transmits control signals, patient- or ventilation-specific parameters and firmware updates to this and, on the other hand, it transmits control signals and processed data to the ventilator and receives patient- or ventilation-specific parameters and firmware updates from this device. It is possible in this way both to operate the ventilator as a function of the EMG signals received and processed and to perform EMG measurements taking ventilation- and/or patient-specific parameters into account. The signal transmission is a wired transmission in this exemplary embodiment, but it is conceivable, in principle, to effect the signal transmission in a wireless manner by means of suitable methods such as Bluetooth, ZigBee or Wi-Fi, the energy being preferably supplied in these cases by means of batteries 13.

On the electrode side, the EMG front end 1 has a terminal 2 for the cable 3 leading to the electrodes 4. To protect the patient, the EMG front end 1 of the EMG measuring system has, further, a defibrillation protection 10, which ensures that a patient leakage current is always lower than 100 µA in a normal situation and lower than 500 µA in an error situation. On the side facing the signal processing unit 8, the EMG front end 1 has, further, a galvanic separation 6, which is embodied by means of a DC-DC coupler with very low coupling capacity.

The EMG measuring system designed according to the present invention with an EMG front end and with a signal processing unit is characterized by an especially low energy consumption. It is to be considered in this connection that the efficiency of the DC-DC coupler is not very high, so that relatively high power losses develop, which cause heat to develop at the couplers. The EMG measuring system described is designed for this reason such that the thermal output does not exceed 300 mW.

Figure 2:
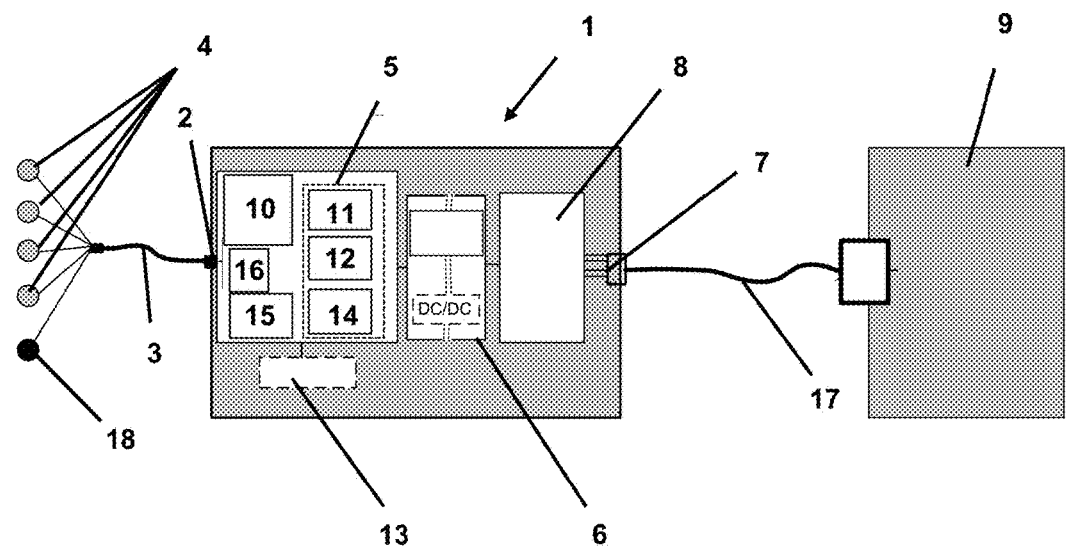
FIG. 2 is a schematic view of the components used.

FIG. 2 shows a concretized view of a system with its components, with which cardiorespiratory monitoring or EMG-based control of a ventilator connected as an external device 9 is achieved in a preferred manner. The EMG measuring system is coupled in this case with a ventilator 9 for the mechanical ventilation of a patient as well as for monitoring the patient. The EMG measuring system has an EMG front end 1 arranged close to the patient, which has a terminal 2 for cables 3, which lead to the EMG electrodes 4. The connection with the electrodes 4 is established by means of an electrode cable 3, preferably a Monolith® cable. Such a Monolith® cable 3 is a single cable, which replaces the multicable systems commonly used hitherto. A total of five electrodes 4 are connected via this cable 3. One electrode pair detects the activity of the diaphragm and one electrode pair detects the activity of the intercostal muscles, while the fifth electrode is used as a reference electrode 16, also called common electrode.

A module 5 is provided in the EMG front end 1 for preprocessing the electric signals delivered by the electrodes 4. This module 5 is always configured as needed using the needed electronic components. The module 5 provided in the EMG front end 1 has, according to this exemplary embodiment, an analog electronic amplifier stage 11 for amplifying the ingoing signals as well as an analog-digital converter 12. Further, a reference amplifier 15 is provided, which is used in combination with a special analog front end single-channel frequency-measuring device 16, a so-called driven right leg architecture. The measuring device 16 can be optimized in an uncomplicated manner, because at least one frequency parameter can be set for all filters, even when a non-linear filter is used. An amplifier 15, designed especially for the use of a driven-leg or driven-right-leg circuit, improves the common mode rejection of the line frequencies of the system. A special function for rapid recovery shortens the duration of the otherwise long transient responses of high-pass filters.

Furthermore, the module 5 has an energy-saving microprocessor 14 for signal preprocessing, by which the fed-back voltage value is calculated for the reference amplifier 15 and the driven-right-leg architecture, a decimation filtering and possibly noise shaping take place, loose electrodes or electrode that have fallen off are identified, the degree of the common mode interference is determined, especially by spectral estimation, the saturation of the amplifier input stage is detected and/or the main transition impedance of the reference electrode 15 is calculated.

Furthermore, a galvanic separation 6 with a DC-DC coupler with very low coupling capacity below 12 pF is provided. Furthermore, a defibrillation protection 10 is provided to protect the connected devices and electronic components.

To transmit raw and status signals to the signal processing unit of the EMG measuring system, the EMG front end 1 has, moreover, an interface 6, which is preferably located in or at the EMG front end 1, but may also be arranged, in principle, at a remote location herefrom.

The signals transmitted are especially EMG raw signals, status signals, such as the validity of the electrode signals, the degree of common mode interference and/or counter and/or check sum or even coding. Further, control signals, such as parameters and firmware, can be transmitted via this interface 7 from the signal processing unit 8 to the EMG front end 1 and in this case especially to the module 5 for signal preprocessing. The transmitted information is information on the patient, especially on whether the patient is an adult, a child or, e.g., a newborn or premature baby, the disease the patient has and whether the patient has a cardiac pacemaker. It is likewise possible to perform needed downloads of the firmware, to form check sums or to update the system via a corresponding interface 7. The signal processing unit 8 of the EMG measuring system, which unit is provided according to the present invention, is preferably located in or at the EMG front end 1, but it is also conceivable, in principle, that the signal processing unit 8 is arranged in a connection cable 17 leading to an external device 9 or in the external device 9, for example, in the form of a plug-in element.

A further preprocessing of the raw signals transmitted from the EMG front end 1 and in this case especially from module 5 for signal preprocessing takes place first in the signal processing unit 8. Especially difference signals are formed in this case. Artifacts, above all residues of cardiac activity (ECG), are removed, slow potentials are removed by means of a baseline filter, as well as enveloping curves are calculated separately for the two difference signals of the respective electrode pairs. Further, the calculation of signal quality indices is performed in the signal processing unit 8, with the inclusion, if available, of the signals that represent airway parameters and are delivered by the ventilator 9, as well as segmenting is performed separately for the two signals of the respective electrode pairs. Furthermore, a decision is made as to which signal shall be triggered, and a calculation of the control signal for triggering-cycling-off and proportional assist is performed.

Thus, the signal processing unit 8 communicates both with the module 5, for signal preprocessing, and with the ventilator 9 bidirectionally. The ventilator 9 receives, at least from time to time, control signals that were generated by the signal processing unit 8 of the EMG measuring system. Displays of the detected measured values on the patient monitor, which displays were produced in a correspondingly suitable manner, and/or settings of the ventilator 9 are made possible in this way.

The signals transmitted to the ventilator 9 are especially EMG enveloping curve signals, ventilation control signals, breathing phase signals, signal quality indices and alarm information as well as further control signals. Since bidirectional communication is provided, signals, parameters and firmware are also transmitted from the connected ventilator 9 to the signal processing unit 8 as needed. These are above all respiratory signals, such as pressure, flow, $CO_2$ content, breathing phase signals and/or alarm information.

The ventilator 9 connected to the EMG measuring system with the monitor integrated therein processes the EMG and control signals received for cardiorespiratory monitoring, optimization of the therapy, e.g., by the optimized setting of the ventilation parameters. Further, the control signals received are used for the automated control of ventilation, for decision assistance and/or for predicting interventions, e.g., extubation.

The communication between the EMG front end 1 via the signal processing unit 8 with the ventilator 9 takes place bidirectionally. The information and energy transmission is embodied as wired transmission according to the exemplary embodiment shown. It is, of course, also conceivable to provide a wireless data trunk, especially for data exchange. LAN, RS232, RS485, SPI, CAN, I2C or analog interfaces with a Baud rate that is higher than 115,200 bps are especially suitable for the wired transmission of information or data. Furthermore, a galvanic separation 6 with at least one DC-DC coupler with very low coupling capacity is provided for uncoupling the EMG measuring system from the ventilator 9 as well as additional devices. The capacity is preferably lower than 10 pF. A low coupling capacity is decisive, because the current that flows through the reference electrode and hence the sensitivity to common mode interferences depend on this capacity.

The EMG measuring system may be supplied with energy in a wired manner. According to the exemplary embodiment described here, a battery 13, which assumes the energy supply as soon as the EMG measuring system is not connected to the power grid, is provided in the front end 1.

While specific embodiments of the invention have been shown and described in detail to illustrate the application of the principles of the invention, it will be understood that the invention may be embodied otherwise without departing from such principles.

APPENDIX

1 EMG front end
2 Terminal
3 Cable
4 EMG electrode
5 EMG module for signal preprocessing
6 Galvanic separation
7 Interface
8 Signal processing unit
9 External device
10 Defibrillation protection
11 Amplifier
12 A/D converter
13 Battery
14 Microprocessor
15 Reference amplifier
16 Analog front-end single-channel frequency-measuring device
17 Connection cable
18 Reference electrode

What is claimed is:

1. An electromyogram (EMG) measuring system comprising:
   a signal processing unit;
   an external device transmitting a signal comprising data to the signal processing unit; and
   at least two electrodes for measuring an EMG signal representing a potential difference created by electrical activity in contraction of a muscle, a muscle fiber and/or in a skin area of a patient, wherein the EMG signal is transmitted from the electrodes to the signal processing unit, and a processed EMG signal, which is transmitted to the at least one external device, is generated in the signal processing unit on the basis of the measured EMG signal, the signal processing unit further processing the signal transmitted from the external device and the signal processing unit generating at least one control signal on the basis of the signal transmitted from the external device, the control signal is generated in the signal processing unit on a basis of the data transmitted by the at least one external device to the signal processing unit for setting at least one time and/or one time interval, in which the measurement of a change in a potential difference takes place.

2. An EMG measuring system in accordance with claim 1, wherein the at least two electrodes are designed as surface electrodes.

3. An EMG measuring system in accordance with claim 1, wherein the control signal generated by the signal processing unit is transmitted to the at least one external device.

4. An EMG measuring system in accordance with claim 1, wherein the signal processing unit and the at least one external device are connected for carrying out a data exchange between the signal processing unit and the at least one external device.

5. An EMG measuring system in accordance with claim 1, further comprising an EMG front end, connected with the electrode, the at least one measured EMG signal being transmitted to the signal processing unit via the EMG front end.

6. An EMG measuring system in accordance with claim 5, wherein the signal processing unit is arranged in or at the EMG front end.

7. An EMG measuring system in accordance with claim 5, wherein a module for preprocessing the at least one measured EMG signal is provided in the EMG front end.

8. An EMG measuring system in accordance with claim 7, wherein the preprocessed measured EMG signal is transmitted to the signal processing unit.

9. An EMG measuring system in accordance with claim 7, wherein a galvanic separation, which has a coupling capacity that is lower than 10 pF to 12 pF, is provided between the module for preprocessing the at least one measured EMG signal and the signal processing unit.

10. An EMG measuring system in accordance with claim 7, wherein:
   the two electrodes also measure electrocardiogram (ECG) signals, the EMG and electrocardiogram (ECG) signals are separated from each other in the module for preprocessing the at least one measured EMG signal.

11. An EMG measuring system in accordance with claim 1, wherein the external device is a ventilator and/or a patient monitor.

12. An EMG measuring system in accordance with claim 11, wherein a ventilator fan of the ventilator and/or a ventilator valve of the ventilator is actuated on the basis of the control signal.

13. An EMG measuring system in accordance with claim 1, wherein the two electrodes also measure electrocardiogram (ECG) signals, the EMG and electrocardiogram (ECG) signals are separated from one another in the signal processing unit.

14. An EMG measuring system in accordance with claim 1, wherein a monitor and/or a keyboard is provided.

15. An EMG measuring system in accordance with claim 1, wherein
a memory cooperates with the signal processing unit, data transmitted from the at least one external device to the signal processing unit is stored in the memory.

16. An EMG measuring system in accordance with claim 15, wherein data relating to a cardiocirculatory system of the patient is stored and/or processed.

17. An EMG measuring system in accordance with claim 1, further comprising at least one of a data interface and an input unit wherein patient-specific information is transmitted to the signal processing unit via a data interface or an input unit.

18. An EMG measuring system in accordance with claim 1, wherein the signal processing unit is arranged in or at an electric cable leading to the external device.

19. An electromyogram (EMG) measuring system comprising:
a signal processing unit;
an external device transmitting a signal to the signal processing unit;
at least two electrodes for measuring a potential difference in a muscle, a muscle fiber and/or in a skin area of a patient, wherein at least one measured signal representing the potential difference is transmitted from the electrodes to the signal processing unit, and a signal, which is transmitted to the at least one external device, is generated in the signal processing unit on a basis of the measured signal, the signal processing unit further processing the signal transmitted from the external device and the signal processing unit generating at least one control signal on a basis of the signal transmitted from the external device;
an EMG front end, connected with the electrode, the at least one measured signal being transmitted to the signal processing unit via the EMG front end, a module for preprocessing the at least one measured signal is provided in the EMG front end, a galvanic separation, which has a coupling capacity that is lower than 30 pF to 40 pF, is provided between the module for preprocessing the at least one measured signal and the signal processing unit.

20. An electromyogram (EMG) measuring system comprising:
a signal processing unit;
an external device transmitting a signal to the signal processing unit;
at least two electrodes for measuring an EMG signal representing a potential difference created by electrical activity in contraction of a muscle, a muscle fiber and/or in a skin area of a patient, wherein the EMG signal is transmitted from the electrodes to the signal processing unit, and a processed EMG signal, which is transmitted to the at least one external device, is generated in the signal processing unit on a basis of the measured EMG signal, the signal processing unit further processing the signal transmitted from the external device and the signal processing unit generating at least one control signal on a basis of the signal transmitted from the external device;
an EMG front end, connected with the electrodes, the at least one measured EMG signal being transmitted to the signal processing unit via the EMG front end;
a module for preprocessing the at least one measured EMG signal is provided in the EMG front end;
a galvanic separation, which has a coupling capacity that is lower than 10 pF to 12 pF, is provided between the module for preprocessing the at least one measured EMG signal and the signal processing unit.

* * * * *